United States Patent [19]

Capuano et al.

[11] 4,294,798

[45] Oct. 13, 1981

[54] SODIUM AMALGAM MONITOR

[75] Inventors: Italo A. Capuano; Patricia A. Turley, both of Orange; Edward W. DuBord, Hamden, all of Conn.

[73] Assignee: Olin Corporation, New Haven, Conn.

[21] Appl. No.: 44,295

[22] Filed: May 31, 1979

[51] Int. Cl.³ .................... G01N 21/00; G01N 31/12
[52] U.S. Cl. ........................................ 422/62; 422/68; 422/80
[58] Field of Search .................. 422/68, 80, 81, 82, 422/100, 62, 76, 90, 111, 116, 119, 211; 23/230 A

[56] References Cited

U.S. PATENT DOCUMENTS

| | | | |
|---|---|---|---|
| 1,156,176 | 10/1915 | Reiche | 422/80 |
| 2,989,377 | 6/1961 | Leisey | 23/230 A |
| 3,014,861 | 12/1961 | Buningh | 422/211 |
| 3,440,016 | 4/1969 | Serfass | 422/81 |
| 3,480,520 | 11/1969 | Smith | 204/1 |
| 3,901,653 | 8/1975 | Jones et al. | 422/62 |
| 4,000,089 | 12/1976 | Senda | 23/232 E |
| 4,095,951 | 6/1978 | DiCola et al. | 422/80 |

Primary Examiner—William F. Smith
Assistant Examiner—Chris Konkol
Attorney, Agent, or Firm—Ralph D'Alessandro; Thomas P. O'Day

[57] ABSTRACT

An apparatus and method are disclosed for automatically monitoring the sodium concentration of a sodium amalgam by means of a wet chemical analysis in which a mineral acid is reacted with a sample of the sodium amalgam to generate an amount of hydrogen gas proportional to the amount of sodium in the amalgam sampled. The amount of such hydrogen gas produced is detected and displayed in units of sodium concentration. A thermal conductivity detector is preferred as the means for determining the amount of hydrogen gas produced.

10 Claims, 3 Drawing Figures

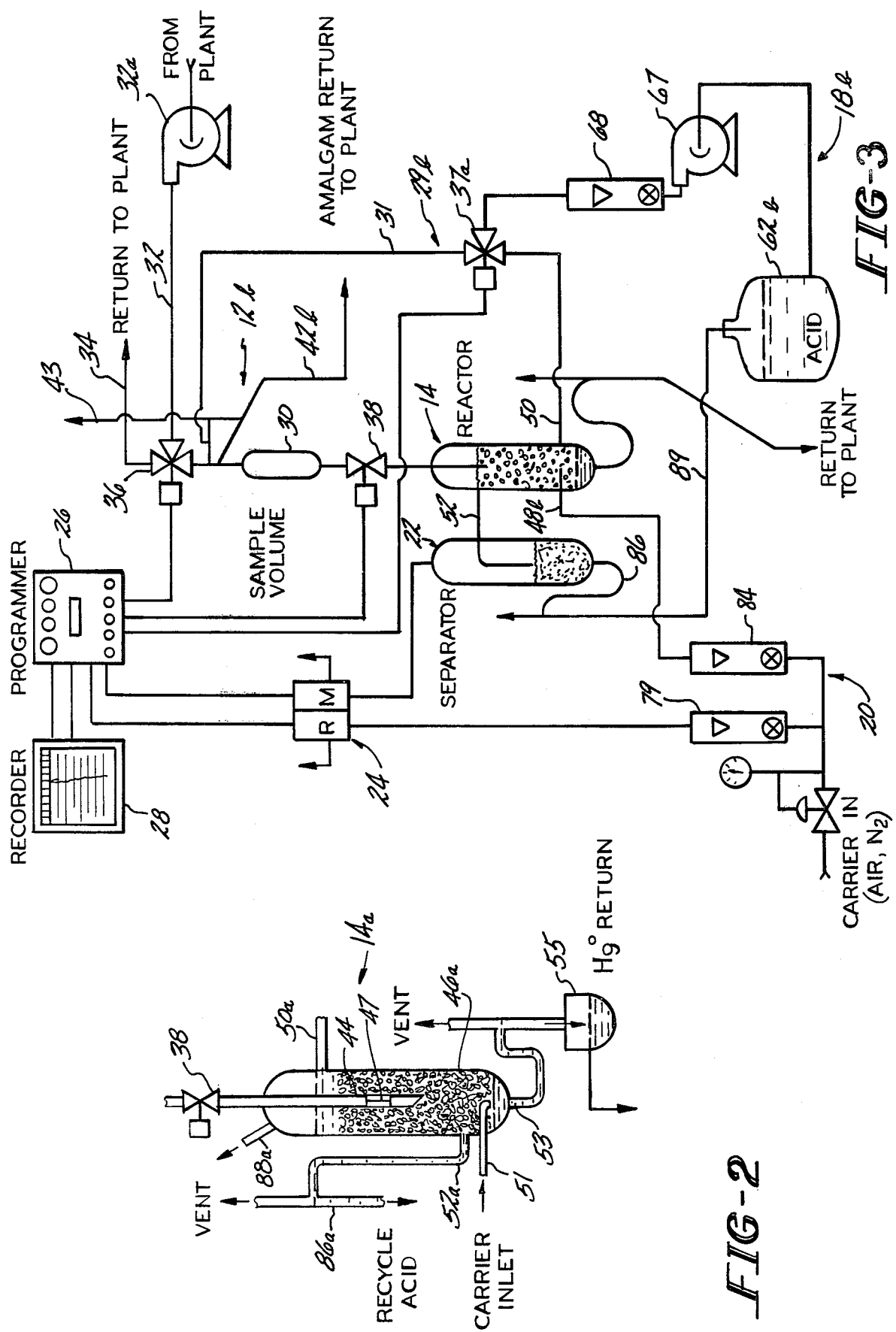

SODIUM AMALGAM MONITOR

This disclosure relates to an amalgam concentration detector method and apparatus and particularly to a detector for automatically monitoring the amount of alkali metal dissolved in the amalgam.

Sodium amalgam (NaHg) is a key intermediate in several important commercial processes. For example, much caustic soda technology is based on the reaction of sodium amalgam and water; similarly, sodium methylate is manufactured from sodium amalgam and methanol, and sodium hydrosulfite is produced by reduction of sulfur dioxide with sodium amalgam.

Industrially, sodium amalgam is produced electrolytically and the amalgam stream piped to processes requiring it as a reactant. The concentrations of other reactants are scaled to sodium concentrations obtainable in practice. Sodium levels are checked intermittently and concentration adjustments made accordingly.

The current method for checking sodium concentration in sodium amalgam is to take a sample of the amalgam source to be measured, transport the sample to a laboratory and run a wet chemistry sodium quantitative analysis on the sample. The current wet chemistry quantitative analysis is to react a given quantity of the sodium amalgam with a given quantity of hydrochloric acid to generate sodium chloride and hydrogen according to the following reaction formula:

$$NaHg + HCl \rightarrow NaCl + Hg^\circ + H_2 \uparrow$$

and then measuring the volume of hydrogen gas evolved. However, the manual analysis is time-consuming and there is a need for a way of more rapidly measuring alkali metal concentrations in amalgam.

Another method proposed is that of U.S. Pat. No. 3,480,520 issued Nov. 25, 1969 to R. E. Smith in which the electrical potential between an alkali metal amalgam having a known concentration of alkali metal in the mercury is compared to the potential of an amalgam having an unknown concentration of alkali metal in the mercury. The amalgams of known and unknown concentrations are separated by a cation exchange membrane to help prevent cross-contamination. However, this reference-electrode-type approach has been found to be susceptible to temperature changes, to require continual recalibration after short intervals and to be highly susceptible to inaccuracies resulting from any leaks in or damage to the membrane within the detector. Thus, the reference electrode method has not proven to be of sufficient commercial reliability and there is still a need for a rapid, alkali metal-in-amalgam detector of greater reliability.

This need is satisfied by the method of the present invention which provides a method of monitoring the sodium concentration in a sodium-mercury amalgam process stream, which comprises the steps of:

(a) automatically withdrawing a sample of said amalgam from said stream;

(b) automatically supplying said withdrawn sample to a reaction zone;

(c) automatically supplying a mineral acid solution to said reaction zone so as to react with said sample to generate hydrogen gas;

(d) automatically generating a signal proportional to the amount of hydrogen gas generated per unit amount of withdrawn sample; and (e) displaying said signal in units of sodium concentration in said amalgam stream.

This need is also satisfied by the apparatus of the present invention which provides:

(a) a reaction chamber;

(b) sample supply means, fluidly connecting said reaction chamber with said sodium amalgam for automatically supplying a selected sample of said sodium amalgam to said reaction chamber;

(c) mineral acid supply means, for automatically supplying a sufficient quantity of mineral acid to said reaction chamber to completely react with and remove any sodium from said amalgam and producing a quantity of hydrogen gas proportional to the amount of sodium in said amalgam;

(d) a liquid-gas separator in fluid communication with said reaction chamber for separating liquid and gaseous reaction products produced by said reaction of said mineral acid with said sodium amalgam;

(e) inert gas supply means, in selective communication with said reaction chamber, for automatically forcing said gaseous reaction products out of said reaction chamber and into said liquid-gas separator;

(f) detector means for determining the amount of hydrogen in the gas fraction from said liquid-gas separator and producing a signal which is indicative of said amount of hydrogen;

(g) a programmer for controlling the order of operation of said sample supply means, mineral acid supply means and inert gas supply means; and (h) display means for visually indicating the amount of said hydrogen in terms of percent sodium in said sodium-mercury amalgam.

A BRIEF DESCRIPTION OF THE DRAWINGS

The advantages of the invention will be better understood by reference to the drawings in conjunction with the following detailed disclosure of the invention, wherein:

FIG. 2 is a schematic diagram combining a reactor with a separator to produce an integral reactor-separator; and FIG. 3 is a schematic diagram of an amalgum monitor utilizing a liquid-acid solution.

A DETAILED DESCRIPTION OF THE DRAWINGS

Figure 1:
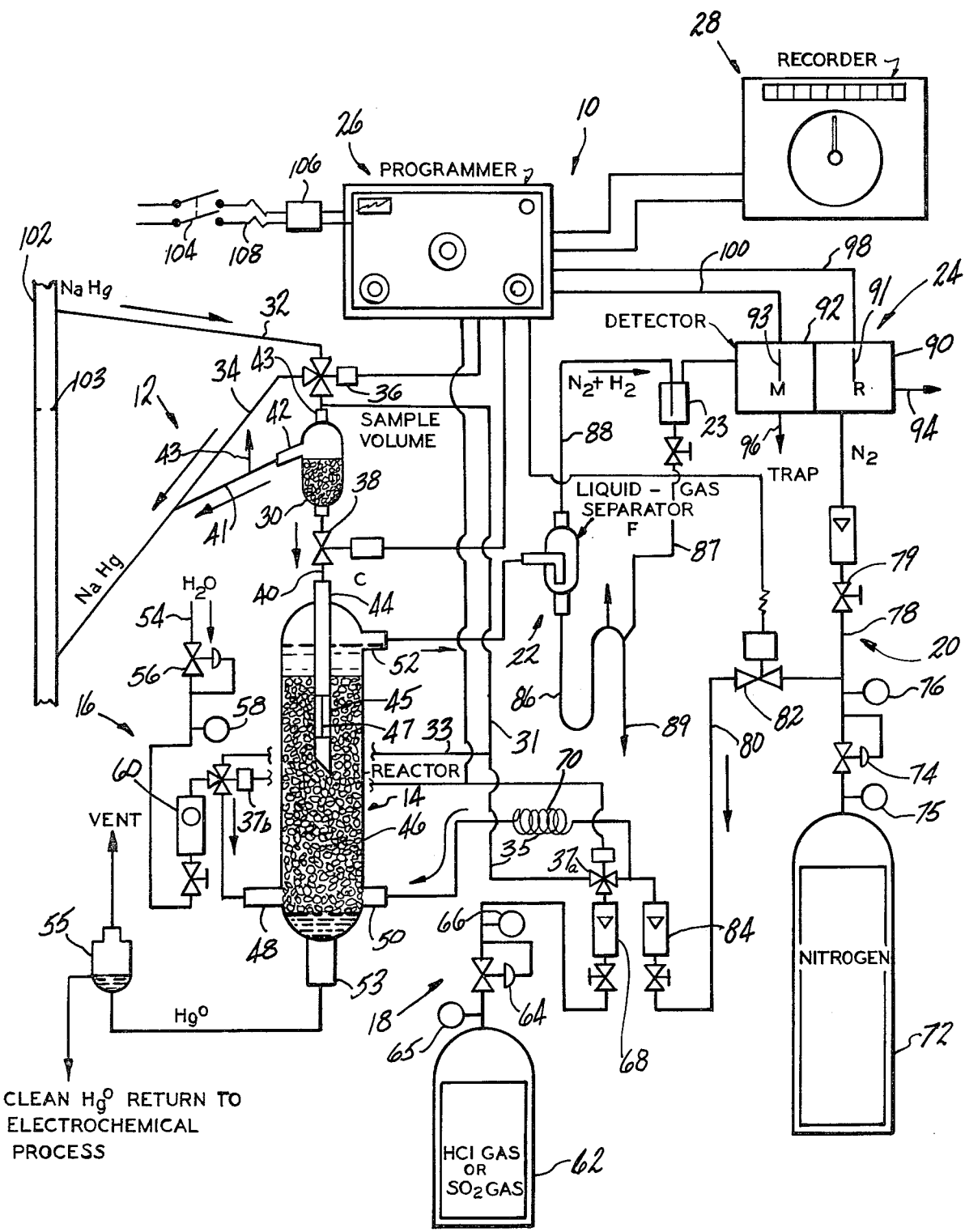
FIG. 1 is a schematic diagram of the preferred amalgum monitor of the invention for rapid intermittent measurement.

FIG. 1 is a schematic diagram of a preferred alkali metal in amalgam monitor 10. Monitor 10 comprises a sampler 12, a reactor 14, a water supplier 16, acid supplier 18, an inert gas supplier 20, a liquid gas separator 22, a thermoconductivity detector 24, a programmer 26, a recorder 28 and a cleansing circuit 29, all electrically or fluidly connected as described below.

Sampler 12 comprises a fixed volume glass sample chamber 30, an amalgam inlet line 32, an amalgam outlet line 34, a first solenoid valve 36, a second solenoid valve 38 and a sample outlet line 40. Inlet 32 and outlet line 34 are connected to the amalgam sample source or "reservoir", such as process stream 102 which is being automatically monitored by monitor 10. Solenoid valve 36 normally connects line 32 to 34 but is automatically activated in response to an activating signal from programmer 26 to connect inlet line 32 to chamber 30. Solenoid 38 is normally closed but is automatically activated in response to an activating signal from programmer 26 to connect chamber 30 to reactor 14. Chamber 30 preferably has an overflow 42 which is connected to outlet line 34 through a return flow line 41. Stream 102 would preferably have differential pressure between its point of connection with line 32 and its point of connection with line 34 so as to force amalgam through lines 32 and 34. An orifice 103 can accomplish this. Line 41 preferably has a vent 43 for use in connection with the cleaning of the feed tube 44, capillary tube 47 and sample chamber 30. Overflow 42 allows any excess amalgam entering sample chamber 30 to flow back to the amalgam process stream 102 via line 34 after sample chamber 30 is filled to the predetermined volume set by the level of overflow 42.

Reactor 14 serves as a flow-through, reactor-scrubber and comprises a feed tube 44 and a reaction chamber 46. Reaction chamber 46 is a hollow glass column with two inlets 48, 50 at its lower end for connection to water supplier 16 and acid supplier 18, respectively, an outlet 52 at its upper end for connection to separator 22 and a drain outlet 53 which is connected to a vented vessel 55 from which mercury could be transferred to some desired location for use. Feed tube 44 acts as a third inlet to reaction chamber 46 and automatically feeds the fixed volume sample from sample chamber 30 into reaction chamber 46 upon the automatic opening of solenoid 38. Feed tube 44 preferably includes a metering means such as a capillary portion 45 with a short length of capillary tubing 47 which meters amalgam from sample chamber 30 into reactor chamber 46 at a slow enough rate to allow all the sodium to be removed by reaction with the acid solution formed from the ingredients from inlets 48 and 50. This tubing 47 is best located below the normal surface level of liquid in chamber 46 so that it will be automatically cleaned by the acid within chamber 46 during the times when valve 38 is closed. The amalgam sample flows downwardly through reaction chamber 46 to drain outlet 53, reacting with acid supplied through inlet 50 to produce hydrogen gas which passes out of outlet 52. Feed tube 44 projects into chamber 46 to some point below outlet 52 so that a sample is not forced out of outlet 52. Reactor chamber 46 is preferably packed with some turbulence-creating material, such as, for example, 6 mm glass spheres, or could have a mechanical agitator to aid in mixing the reactants from inlets 48, 50 with the sample from feed tube 44.

Water supplier 16 comprises a continuous flow, regulated pressure, regulated flow rate water supply system and thus comprises in sequence a water inlet line 54, a pressure regulator valve 56, a pressure gauge 58 and a rotameter flow rate valve 60. Water supplier 16 serves to provide to inlet 48 the solvent for the reaction in chamber 46 between sodium amalgam and mineral acid from acid supply 18. Water inlet line 54 can be connected to a source of pressurized distilled water. If it is certain that such source is at constant pressure, then regulator valve 56 could be omitted, although as a precaution it is preferred that valve 56 be present even then.

If an aqueous acid solution is provided by acid supply 18, water supplier 16 could be eliminated. However, even then it is possible to have water supplier 16 so that an operator has the option of switching to a gaseous acid supply so that acid is continuously generated.

Acid supply 18 comprises a mineral acid reservoir such as a tank 62 of compressed HCl or $SO_2$ gas with associated gas pressure regulator valve 64 and pressure gauges 65 and 66 connected to inlet 50 through a flow rate control valve such as rotameter valve 68 and mixer 70. Any noninterfering acid could be used, such as sulfuric acid or even an organic acid, although organic acids are somewhat weak. If an aqueous acid solution is used as the acid reservoir, an acid-resistant pump is added between the acid reservoir and valve 68. Also, if an aqueous acid solution is used, water supply 16 could be omitted if the acid solution already had sufficient water. Valves 64 and 68 are set so as to provide a continuous flow of acid to inlet 50. The flow of acid from acid supply 18 and water from water supply 16 is preferably continuous so that the molar concentration of acid in acid-water reactant mixture flowing from inlets 48 and 50 upward through the reaction chamber 46 to outlet 52 is always above the level where 100 percent of the metallic sodium in the amalgam is reacted during the time the amalgam falls from feed tube 44 to outlet 53. For HCl, that level was found to be 1.2 percent or 0.38 molar when using a 3.7 ml amalgam sample containing 0.1 percent sodium and a 50 ml reaction chamber. An acid concentration within the range of from about 1 percent to about 99 percent could be used. An acid concentration within the range of about 5 percent to about 40 percent is preferred so that a smaller reaction chamber without mechanical stirrers can be used. Acid-producing gas flow rates, $H_2O$ flow rates, the volume of liquid acid in the reactor, the sample (Hg) size and the contact time between the amalgam and aqueous acid phases (which is determined by the length of the reactor and the size of the packing) establish the minimum acid concentration requirements for any specific version of monitor 10. In terms of the stoichiometric amount, at least the stoichiometric amount and preferably an amount within the range of from about 8 to about 200 times the stoichiometric amount of acid is supplied to reactor 14. If a sulfuric acid solution is to be produced, $SO_2$ gas could be automatically reacted with water and air or oxygen and the resultant $H_2SO_4$ solution fed to reaction chamber 46. The flow of acid-water reactant mixture into chamber 46 is thus automatic in the sense that no manual control is necessary because the flow is continuous.

In order to serve as reference gas and carrier gas for detector 24, an inert carrier gas such as nitrogen gas is supplied for selected intervals. The nitrogen gas is supplied by an inert gas supply such as gas supply 20 which comprises a compressed nitrogen gas tank 72 with a conventional regulator valve 74 and pressure gauges 75 and 76, a reference flow line 78, a carrier gas flow line 80. Flow line 78 connects valve 74 and detector 24 through a rotameter valve 79. Flow line 80 connects mixer 70 and vlave 74. In line 80 is optionally placed a normally open two-way solenoid valve 82 and a flow rate control such as a rotameter valve 84, so that a preset flow of inert gas is fed to mixer 70 upon the opening of solenoid valve 82.

Liquid-gas separator 22 is any conventional means for separating the gas and liquid flow from outlet 52 into its gas and liquid components into a liquid fraction which is passed through a vented drain line 86 to a drain 89 and a gas fraction which is fed through a detector inlet line 88 to detector 24. Although in the FIGURE separator 22 is shown above the level of outlet 52, it would actually be lower than outlet 52 so that acid would drain into separator 22 from outlet 52 by gravity. If an aqueous acid supply reservoir is used, the drain line 86 drains back into the acid supply. A second liquid gas separator or "vapor trap" 23 could also be added in line 88 to further separate gas from possible residual traces of liquid. A second drain line 87 leading into drain line 86 can drain this second separator through the valve provided in drain line 87 when and if it becomes necessary.

It would also be possible to combine reactor 14 with separator 22 as in FIG. 2 to produce an integral reactor-separator 14a. Reactor-separator 14a has a chamber 46a, feed tube 44, acid inlet 50a, a carrier gas inlet 51, an amalgam outlet 53, a vented vessel 55, acid outlet 52a, a vented drain line 86a and a gas fraction outlet 88a. Acid inlet 50a is located about four-fifths of the way up a side of chamber 46a at about the surface level of the liquid within chamber 46a. Acid outlet 52a begins about one-fifth of the way up the side of chamber 46a and extends upwardly to a height which determines the level of the liquid in chamber 46a and then downwardly through a vented drain line 86a to an acid reservoir such as in FIG. 3. Feed tube 44 and capillary tube 47 have already been described above. Gas outlet 88a communicates with chamber 46a near the top thereof to receive the carrier gas and any gaseous reaction product such as hydrogen. Carrier gas inlet 48a communicates with reaction chamber 46 just above the level of amalgam in drain outlet 53 so that upward gas flow helps agitate the liquid in chamber 46.

Thermal conductivity detector 24 is similar to conventional two sensor devices and has a reference chamber 90 containing a reference sensor 91 and a measurement chamber 92 containing a measuring sensor 93. However, it is preferable to have detector 24, unlike conventional detectors, have a non-corrosive, diffusion resistant, thermally stable plastic in order to handle acidic gases and to last in a corrosive environment such as in a chlor-alkali plant. Glass covered thermistors are the preferred sensors as they are more acid resistant than wire loops or resistors. Reference flow line 78 supplies inert gas such as nitrogen to reference chamber 90 while detector inlet line 88 supplies the gas fraction from separators 22 and 23. Gas is exhausted from reference chamber 90 through a reference exhaust 94 and from measurement chamber 92 through a measurement exhaust 96. The flow rates through chambers 90 and 92 are regulated by valves 79 and 84, the flow through chamber 92 also being increased by the amount of any hydrogen gas generated by reactor 14. A heater (not shown) could be added to detector 24 so that the gases being measured are at the same temperature for added precision, as the cooling effect of the gases depends on their temperature.

Programmer 26 can be any automatic means for sequencing the operation of solenoid valves 36, 37, 38 and 82 so as to perform the analysis. A multiple cam timer is preferable, such as for example, a Model MC-6-6 Timer, C-12, 12 rpm multicam timer by Industrial Timer. The multiple cam switch timer could thus be patterned after the multiple cam switch disclosed in commonly owned U.S. Pat. No. 4,151,255 filed Oct. 11, 1977 by I. A. Capuano and E. G. Miller, entitled "pH Monitor With Automatic Buffer Standardization", except that fewer cams would be required. In particular, only four or five cams are needed although six cams are preferred so that extra operations could be added later, if desired. The programmer 26 receives signals from the reference sensor 91 and measurement sensor 93 which pass through detector signal lines 98 and 100 to programmer 26 and from programmer 26 to recorder 28. The detector signals can be amplified, if desired, either in programmer 26, recorder 28 or both.

Programmer 26 also includes a power switch 104 for selectively connecting or disconnecting programmer 26 and recorder 28 from an external or internal power source. Programmer 26 can include a timer 106 switch for automatically operating monitor 10 for only intermittent periods, if desired. Programmer 26 would preferably have a fuse 108 to prevent electrical damage, a zero potentiometer to balance the detector bridge.

Recorder 28 is a conventional disc or chart recorder for giving a visual readout of the detector signal. The detector signal could also be supplied to a visual or sound alarm device or into some automatic process control device related to the amalgam source being measured.

Cleansing circuit 29 comprises solenoid valves 37a and 37b, liquid-acid supply line 31, cleansing water supply line 33 and cleansing acid supply line 35. If acid supply 18 is modified to supply aqueous acid solution to valve 68, then line 33 and valve 37b could be omitted if no additional water is needed for the cleansing procedure. Valves 37a and 37b are normally closed solenoid valves which are simultaneously, automatically, intermittently activated by a signal from programmer 26 so as to allow flow through lines 33 and 35 to line 31 and from line 31 to line 32 immediately below valve 36. Valves 37a and 37b are preferably activated by programmer 26 during the time valve 38 is also being activated by programmer 26 so that the acid flows through chamber 30 and feed tube 44 into chamber 46. Also, valves 37a and 37b are preferably closed before chamber 30 fills so that acid is not dumped into line 34. The acid supplied by line 31 thus passes through chamber 30, valve 38, feed tube 44 and capillary 47 to cleanse the sampling system and prevent clogging. If acid would not be harmful to stream 102, then valve 33 could stay open for longer periods so as to clean outlet 42 and line 41 as well. Valves 37a and 37b could alternatively be manually controlled since the cleansing operation is normally needed only intermittently, however, to help eliminate human error or forgetfulness, automatically timed solenoid valves are preferred. If a recirculated liquid-acid solution were used instead of a constantly generated gas-water acid solution then line 33 and valve 37b could be deleted. A system using a liquid-acid solution is seen in FIG. 3.

Monitor 10 is preferably built of chlorine, acid and caustic resistant components so that it is able to withstand the process environment in which it is to be used. The monitor may include an auto-zeroing feature to correct for any baseline drift due to thermistor decay or other causes so that a nitrogen carrier stream with some hydrogen chloride gas, such as would result from either no sample or no sodium in the mercury, would produce a zero "baseline" reading.

The operation of monitor 10 of FIG. 1 will now be described. It is submitted that the above description already has made such operation clear, however, the following description of the operation is provided for further clarification. Monitor 10 can be utilized to monitor the sodium concentration in a sodium amalgam which can be supplied through amalgam inlet line 32 from any source that is desired. However, monitor 10 is particularly suited for use in monitoring the sodium concentration in an amalgam process stream such as stream 102 of FIG. 1. Amalgam from stream 102 is partially diverted through inlet line 32, valve 36 and outlet line 34 in order that the amalgam can be sampled for measurement by monitor 10. Valve 36 is normally open to flow between lines 32 and 34 and is selectively closeable to force amalgam to flow from inlet line 32 to outlet line 34 through sample chamber 30 and overflow 42. Since sample chamber 30 is of a fixed volume and overflow 42 must be at some level above the bottom of chamber 30, a fixed volume will be trapped in that portion of sample chamber 30 below overflow 42. When a sufficient time has passed to allow sample chamber 30 to be filled, programmer 26 signals valve 36 to close by interrupting current flow to valve 36 to allow it to return to its normally closed position, and allow flow from inlet line 32 directly to outlet line 34. After valve 36 is closed, programmer 26 optionally sends an activating signal to optional valve 82 to stop flow of inert gas through line 80 to chamber 46 and then sends an activating signal to solenoid valve 38 causing valve 38 to move from its normally closed position to an open position thereby allowing the sample trapped in sample chamber 30 to be dumped into reaction chamber 46. After a sufficient time to allow sample chamber 30 to fully drain, programmer 26 interrupts the circuit to solenoid valve 38 causing it to move back to its normally closed position and thereby blocking any flow from reaction chamber 46 into sample chamber 30. Water supplier 16 is continuously operated to supply water at a given pressure set by regulator valve 56 and a given flow rate set by flow rate valve 60 to reaction chamber 46. This water serves as the solvent for the reaction in reactor 14. Acid supply 18 is similarly continuously operated to supply mineral acid, such as for example hydrogen chloride gas, at a given pressure set by regulator valve 64 and a given flow rate set by valve 68 through mixer 70 to reaction chamber 46.

Inert gas supply 20 is continuously operated to supply inert gas at a given pressure set by regulator valve 74 and a given flow rate set by valve 79 to the reference chamber 90 of detector 24. Gas supply 20 is also automatically operable to supply nitrogen gas at the given pressure set by regulator valve 74 and a flow rate set by valve 84 through mixer 70 to reaction chamber 46. Mixer 70 serves to mix the continuously supplied acid with the intermittently or continuously supplied inert gas from gas supply 20 and provide the mixture resulting therefrom to reaction chamber 46. This automatically programmed intermittent or continuous flow of inert gas serves as a carrier which both carries the mineral acid to reaction chamber 46 and the hydrogen gas produced by the reaction within chamber 46 to liquid-gas separator 22 and from liquid-gas separator 22 to measurement chamber 92 of detector 24. The continuously supplied inert gas flowing to reference chamber 90 serves to provide a reference against which the thermal conductivity of the mixture of inert gas and hydrogen gas flowing through measurement chamber 92 can be compared.

Once valve 38 has been closed and a sufficient time has passed to allow the continuously supplied mineral acid to react with the sample within reactor chamber 46, programmer 26 automatically stops sending an activating signal to optional solenoid valve 82 to thereby reopen valve 82 to cause inert gas to flow through line 80, valve 84, mixer 70 and inlet 50 to reaction chamber 46. The inert gas then flows through reaction chamber 46 and carries any hydrogen gas formed out through outlet 52 to liquid-gas separator 22, as above described. The inert gas and hydrogen gas mixture continues to flow from liquid-gas separator 22 through optional separator 23 and measurement chamber 92 to exhaust 96. During the time this mixture flows through measurement chamber 92, it acts to cool sensor 93, thereby lowering the resistance of sensor 93 and hence causing more current to flow through line 100 than otherwise. The cooling effect of hydrogen gas is known to be greater than the cooling effect of pure nitrogen gas so that nitrogen gas is preferred as the inert gas. However, any other gas which has a different thermal conductivity than hydrogen and which is not reactive with hydrogen gas, such as air and oxygen, can be used as the inert gas in place of nitrogen.

Liquid-gas separator 22 is preferably a glass bulb fitted with a liquid leg (trap) to serve as a lower seal. In such a separator, the acid and inert "carrier" gas enter through the side of separator 22 into a down-facing tube. The acid falls to the bottom of the bulb and the gas exits at the top of the bulb. Separator 22 serves to separate out the liquid which is carried from reaction chamber 46 by the inert carrier gas through outlet 52 into liquid-gas separator 22. Separator 22 thus divides the aqueous acid, inert gas and hydrogen gas mixture into a gas fraction and a liquid fraction. The liquid fraction drains through a vented drain line 86 to a drain 89 while the gas fraction passes through line 88 to optional separator 23 and from separator 23 through measurement chamber 92 to exhaust 96. Optional separator 23 is similar to separator 22 except that it has a drain line 87 which is valved so that periodically any possible liquid accumulated in separator 23 can be drained into vented drain line 86. Flow through drain line 87 is normally closed since the flow from line 88 into separator 23 normally contains little or no liquid. If drain line 87 was not closed, the hydrogen gas from reaction chamber 46 and separator 22 might escape through line 87 to vented drain line 86 and thus be lost from the measurement. In order to drain any accumulated liquid in separator 23, line 87 is periodically opened to allow accumulated liquid to fall into vented drain line 86. Detector 24, as noted above, is a thermal conductivity detector. Such detectors are well known in the analytical chemical art as being useful to check for gases or liquids having different thermal conductivity. Preferred as detector 24 is a dual glass covered sensor thermistor-type thermal conductivity detector wired in a Wheatstone Bridge electrical configuration. Gas from lines 78 and 88 flow past sensors 91 and 93 at approximately the same rate. An imbalance occurs between the two detector elements when the hydrogen from the amalgam-acid reaction flows past sensor 93 while gas from line 78 is flowing past sensor 91. This imbalance is measured as a change in voltage by programmer 26 where it is amplified for external recording by recorder 28.

Programmer 26 serves to control the sequence of operations of the monitor 10 and particularly controls solenoid valves 36, 38 and 82 so that the sample is properly and completely obtained and supplied to reactor 14 and so that the reaction is allowed to occur within chamber 46 prior to chamber 46 being flushed with inert gas from line 80. Programmer 26 can also contain amplifiers, if necessary, to convert the signal from sensors 91 and 93 into a sufficiently strong signal to operate recorder 28 and can also contain electrical circuitry to store the peak height or peak area of the signal indication (e.g., voltage imbalance). Also, a conventional auto-zero adjustment means could be provided to correct for any baseline drift of the converted signals from sensors 91 and 93.

Recorder 28 can be any suitable recorder that will provide a visual record of the signals supplied to it by programmer 26 and electrodes 91 and 93. Such recorders are readily available commercially and therefore the detailed structure of recorder 28 will not be supplied here since such details are not necessary to carrying out the invention in the best manner known.

Since the reaction within reaction chamber 46 serves to remove metallic sodium from the sodium amalgam, relatively pure mercury results. This mercury drains through reaction chamber 46 into drain outlet 53 and out of drain outlet 53. This mercury can be returned through a return line to the process stream 102 or can be supplied to any other desired process or can even be stored. It will be understood that when the sample is dumped from sample chamber 30 into reaction chamber 46, the amalgam is not retained within reaction chamber 46, but rather is allowed to flow downwardly through chamber 46 to drain outlet 53. The reason for this is that the reaction of the mineral acid supplied by acid supply 18 with the amalgam is sufficiently fast and the chamber length sufficiently long that substantially all sodium content in the amalgam is removed during the relatively brief time that it takes the amalgam sample to pass through reaction chamber 46 to drain outlet 53. If desired, the drain outlet 53 could be provided with a valve in order to retain the amalgam in reaction chamber 46 for additional time to allow the reaction to progress further. However, it has been found that for sodium amalgam there is apparently no need for such a valve or such retention of the amalgam. Reaction chamber 46 can instead be packed with glass spheres or other nonreactive, turbulence-creating objects so as to force the amalgam to flow along a tortuous path between tube 44 and drain outlet 53 to give additional time and increase amalgam-acid contact area to help the reaction to occur within the reaction chamber 46.

A recirculating acid solution supplied through a pump to valve 68 is the best mode currently envisioned for use in acid supply 18 and is an alternative within the scope of the invention to acid supply 18 and water supply 16. If such a recirculating acid solution was utilized, drain line 86 could lead to a reservoir in the acid supply in which such solution was contained in order that the solution be reused. Also, if a recirculating acid solution was utilized, water supplier 16 could be eliminated since the acid solution would already contain a predetermined proportion of water. Based on preliminary calculations, a 4 liter container of 15 percent HCl should be able to perform about 7,000 analyses of samples containing 0.1 percent sodium concentration before being exhausted, based on a 3.7 milliliter sample volume of amalgam. If monitor 10 were run continuously to provide a continuous sample to reaction chamber 46, acid supply 18 and water supply 16 would be preferred so that acid could be continuously generated. If the sampling were continuous, it would not be necessary to have a sample chamber 30 but rather both the sample chamber 30 and valves 36, 38 and 82 could be eliminated. However, even if the sampling was continuous, it would be preferable to retain sample chamber 30 and valves 36, 38 and 82 with proper sample bypasses (not shown) to allow continuous flow of sample to reactor 14 in order to have the option of switching to intermittent sampling, if the need arose.

The amount of acid used by monitor 10 is a variable, depending on the design of reactor 14. Sodium amalgam will completely react with less acid or even just water if sufficient agitation is present, so a mechanical agitator could be added to reactor 14 if desired. The glass beads provide sufficient agitation for relatively low acid concentration levels and operate without additional power consumption or susceptibility to mechanical breakdown of a mechanical agitator and are thus preferred.

Since amalgam is known for its tendency to build up and deposit on the linings of components through which it flows, it is desirable to intermittently clean components whose operation could be hindered by such build-up. Automatic cleansing circuit 29 is designed to alleviate this problem. Another manual cleansing alternate method will now be described. A suction bulb applied to vent 43, after blocking fluid communicating between vent 43 and line 34 utilizing another valve in line 41 (not shown) downstream of vent 42 could draw acid from reaction chamber 46 into sample chamber 30 to clean deposits from chamber 30. This cleansing operation would also further clean capillary 47.

A monitor 10b, which is a simplified version of monitor 10, is shown in FIG. 3. Unless otherwise indicated, the reference numbers common to FIGS. 1 and 3 indicate identical items functioning in the same manner. Monitor 10b comprises sampler 12b, reactor 14, acid supplier 18b, inert gas supplier 20, liquid-gas separator 22, detector 24, programmer 26, recorder 28 and cleansing circuit 29b. Reactor 14 and gas supplier 20 are the same as in monitor 10 (FIG. 1) except that carrier gas flows directly to inlet 48 and mixer 70 is thus eliminated. Also, inlet 48b does not lead to a water supplier since acid supplier 18b provides the proper amount of water. Separator 22, detector 24, programmer 26 and recorder 28 are the same for monitor 10b as for monitor 10. Referring to both FIGS. 1 and 3, monitor 10b is simpler than monitor 10 because water supplier 16 is not needed. Also, optional vapor trap 23, optional carrier gas shut-off valve 82, acid gas pressure gauges 65 and 66, acid gas valve 64 and acid gas tank 62 are eliminated. Acid reservoir 62b and circulator 67 normally provide the acid supply through valve 37a at the flow rate set by rotameter valve 68. In order to assist sampling, an amalgam pump 32a is interposed in line 32. Line 42b is returned separately from line 34 in monitor 10b. Valve 37a in monitor 10b automatically activates to block acid flow to inlet 50 and the flow of cleansing acid through line 31 to sample chamber 30 at selected intervals from about once per 40 minutes to about once per five hours. Since some acid from circuit 29b may remain in chamber 30 following cleansing, the first few readings of recorder 28 after cleansing may be lower than actual. Line 31 is preferably vented by connection thereof to vent 43.

While the invention has been disclosed in terms of a preferred method and apparatus and an alternate method and apparatus, it will be understood that other alternates will be apparent to those skilled in the art without departing from the scope of the invention and the claims below are intended to cover any such alternates.

There will now be given in conclusion an example in more precise terms of the operation of the invention for purposes of illustration only.

EXAMPLE

A monitor was constructed according to FIG. 1. Sample chamber 30 was designed to trap a 3.7 milliliter amalgam sample. At 0.1 percent Na concentration in the amalgam, this gave 2 milliequivalents of sodium. At least 16 milliequivalents of hydrogen chloride gas were supplied by acid supply 18 to the reactor chamber 46 to react with the sample as the sample was allowed to pass through the reactor chamber 46.

At set time intervals of as short as 2.5 minutes, valve 36 was opened to fill sample chamber 30 and then reclosed. Then valve 82 was closed for a few seconds while valve 38 was opened and the amalgam sample was reacted with the acid contained within chamber 46. Upon completion of the reaction, valve 82 was reopened and any hydrogen gas produced by the reaction was swept by nitrogen passing through valve 82 and chamber 46 to a liquid-gas phase separator 22, vapor-trap type separator 23 and then thermoconductivity detector 24. The detector signal from electrodes 91 and 93 was amplified and transmitted to recorder 28 and was read directly from a chart trace. Peak heights rather than peak areas were measured since the former was insensitive to changes in the nitrogen flow rate over the range 200–800 cc/min. Programmer 26 was a three-cam timer controlling valves 36, 38 and 82. The flow rates for water, HCl gas and nitrogen gas were:
Water—50 cc/min.
HCl—600 cc/min. of air equivalent
$N_2$—400cc/min.

Amalgams of varying sodium concentration were checked both by the monitor 10 and by the standard laboratory method of reacting amalgam with acid and measuring the hydrogen generated. The results, given in Table I below agreed to within 2 percent.

TABLE I

| No. of Determinations | NaHg Analyzer Precision | | |
|---|---|---|---|
| | Wet Std. Method | Novel Analyzer | Difference |
| 1 | 0.0416 | 0.0417 | −0.0001 |
| 2 | 0.0466 | 0.0485 | 0.0019 |
| 3 | 0.0450 | 0.0446 | 0.0004 |
| 4 | 0.0436 | 0.0440 | 0.0004 |
| 5 | 0.0449 | 0.0431 | 0.0018 |
| 6 | 0.0453 | 0.0465 | −0.0012 |
| 7 | 0.0440 | 0.0432 | 0.0008 |
| 8 | 0.0466 | 0.0460 | 0.0006 |
| 9 | 0.0450 | 0.0440 | 0.0010 |

No. of observation = 9
Mean Average Deviation = 0.0009

What is claimed is:

1. An apparatus for automatically monitoring sodium concentration in a sodium-mercury amalgam, which comprises:
   (a) a reactor;
   (b) sample supply means positioned above said reactor, fluidly connecting said reactor with said sodium amalgam for automatically supplying a selected sample of said sodium-mercury amalgam to said reactor;
   (c) acid supply means containing acid connected to the lower end of said reactor for automatically supplying a sufficient quantity of acid to said reactor to completely react with and remove any metallic sodium from said sample and producing a quantity of hydrogen gas proportional to the amount of sodium in said sample;
   (d) a liquid-gas separator located at the upper end of said reactor in fluid communication with said reaction chamber, for separating liquid and gaseous reaction products produced by said reaction of said mineral acid with said sample;
   (e) inert gas supply means containing inert gas connected to the lower end of said reactor in selective communication with said reaction chamber, for automatically forcing said gaseous reaction products out of said reactor and into said liquid-gas separator;
   (f) a reactor outlet for mercury removal located at the bottom of said reactor;
   (g) detector means for determining the amount of hydrogen in the gas fraction from said liquid-gas separator and producing a signal which is indicative of said amount of hydrogen;
   (h) a programmer means for controlling the order of operation of said sample supply means, mineral acid supply means and inert gas supply means; and
   (i) display means, for providing a visual indication of the amount of said quantity of hydrogen in terms of percent sodium concentration in said sample.

2. The apparatus of claim 1 wherein said detector means is a thermal conductivity detector having separate reference and measurement sensors.

3. The apparatus of claim 1 wherein said sodium-mercury amalgam is contained in and flowing through a flow line and said sample supply means includes an inlet line from said flow line and an outlet line to said flow line, said outlet and inlet lines being fluidly connected through a normally open sampling valve which can be selectively closed to direct a sample of said amalgam through said sample supply means to said reactor.

4. The apparatus of claim 3 wherein said sample supply means includes a fixed volume sample chamber so that a sample of fixed volume is supplied to said reaction chamber.

5. The apparatus of claim 3 wherein said reactor comprises a hollow column at least partially packed with an inert, turbulence-creating material.

6. The apparatus of claim 1, wherein said reaction chamber comprises:
   (a) a reaction chamber having at least one inlet adjacent to the lower end of said reaction chamber and in fluid communication with said acid supply means, at least one outlet in fluid communication with said liquid-gas separator and located at a height on said reaction chamber above the location of said inlet so as to maintain a quantity of acid between said inlet and outlet; and
   (b) a feed tube having a capillary for metering said sample from said sample supply means into said reaction chamber, said capillary being located below said outlet so that said capillary is exposed to and cleaned by said acid.

7. The apparatus of claim 1 wherein said sample supply means is a means for continuously supplying said amalgam to said reaction chamber and said acid supply means is a means for continuously generating and supplying acid to said reaction chamber in a sufficient quantity to fully react with any sodium in said supplied amalgam.

8. The apparatus of claim 1 further comprising a recorder for recording said indication of sodium concentration in said sampled amalgam.

9. The apparatus of claim 1 wherein said separator forms an integral part of said reactor.

10. An apparatus for automatically monitoring sodium concentration in a sodium-mercury amalgam, which comprises:
(a) a reactor;
(b) sample supply means positioned above said reactor, fluidly connecting said reactor with said sodium amalgam for automatically supplying a selected sample of said sodium-mercury amalgam to said reactor;
(c) acid supply means at the lower end of said reactor for automatically supplying a sufficient quantity of acid to said reactor to completely react with and remove any metallic sodium from said sample and producing a quantity of hydrogen gas proportional to the amount of sodium in said sample;
(d) a liquid-gas separator located at the upper end of said reactor in fluid communication with said reaction chamber, for separating liquid and gaseous reaction products produced by said reaction of said mineral acid with said sample;
(e) inert gas supply means located at the lower end of said reactor in selective communication with said reaction chamber, for automatically forcing said gaseous reaction products out of said reactor and into said liquid-gas separator;
(f) a reactor outlet for mercury removal located at the bottom of said reactor;
(g) detector means for determining the amount of hydrogen in the gas fraction from said liquid-gas separator and producing a signal which is indicative of said amount of hydrogen;
(h) a programmer means for controlling the order of operation of said sample supply means, mineral acid supply means and inert gas supply means;
(i) display means, for providing a visual indication of the amount of said quantity of hydrogen in terms of percent sodium concentration in said sample; and
(j) cleansing means for automatically intermittently supplying acid from said acid supply means to said sample supply means to cleanse amalgam deposits therefrom.

* * * * *